United States Patent [19]

Liang

[11] Patent Number: 5,132,311
[45] Date of Patent: Jul. 21, 1992

[54] CYANOQUANIDINE TYPE III ANTIARRHYTHMIC AGENTS AND USE

[75] Inventor: Chi-Dean Liang, Glenview, Ill.

[73] Assignee: G. D. Searle & Co., Chicago, Ill.

[21] Appl. No.: 737,963

[22] Filed: Jul. 30, 1991

Related U.S. Application Data

[63] Continuation-in-part of Ser. No. 545,250, Jun. 27, 1990.

[51] Int. Cl.$^5$ .................. A61K 31/445; A61K 31/47; C07D 401/12
[52] U.S. Cl. .................................... 514/307; 514/323; 546/145; 546/201
[58] Field of Search ................ 546/145, 201; 514/307, 514/323

[56] References Cited

U.S. PATENT DOCUMENTS 4,925,850  5/1990  George et al. ...................... 546/146

OTHER PUBLICATIONS

Cornu et al, *Chemical Abstracts*, vol. 105 (1986) No. 42652f.

*Primary Examiner*—Robert W. Ramsuer
*Attorney, Agent, or Firm*—Joy Ann Serauskas; Paul D. Matukaitis

[57] ABSTRACT

Cyanoguanidines which have activity as Class III antiarrhythmic agents, acting by prolonging cardiac action potential repolarization. The invention further provides for compositions incorporating the compounds and methods of their use, as well as providing for pharmaceutically acceptable salts of the compounds.

14 Claims, No Drawings

CYANOQUANIDINE TYPE III ANTIARRHYTHMIC AGENTS AND USE

This application is a continuation-in-part of Ser. No. 07/545,250, filed Jun. 27, 1990, now pending.

BACKGROUND OF THE INVENTION

The present invention provides novel compounds, novel compositions, methods of their use and methods of their manufacture, such compounds generally pharmacologically useful in the treatment of cardiac arrhythmias. The aforementioned pharmacologic activities are useful in the treatment of mammals. More specifically, the compounds of the present invention are orally active Class III antiarrhythmic agents which, by effectively prolonging repolarization of a cardiac cell action potential, can be used effectively to treat certain cardiac arrhythmias. At the present time, there is a need in the area of cardiology therapy for such an agent.

Antiarrhythmic drugs have been grouped together according to the pattern of electrophysiological effects that they produce and/or their presumed mechanisms of action. Thus, Class I antiarrhythmic agents are characterized by being sodium channel blockers, Class II antiarrhythmic agents are beta-adrenergic blockers, Class III antiarrhythmic agents prolong repolarization and Class IV antiarrhythmic agents are calcium channel blockers.

Currently, there are very few Class III antiarrhythmic agents available for therapeutic use. Among them is bretylium. Bretylium's usefulness is limited however, and currently its therapeutic use is reserved for life-threatening ventricular arrhythmias that are refractory to therapy. Thus, bretylium's use is generally confined to intensive care units. It is an object of this invention to provide Class III antiarrhythmic agents of broader therapeutic use than existing Class III antiarrhythmic agents. There is a need in the area of cardiovascular therapeutics for an agent which has broader clinical usefulness. The compounds of the present invention meet this need in the art by providing for orally active therapeutic agents for the treatment of cardiac arrhythmias.

SUMMARY OF THE INVENTION

The present invention relates to a class of compounds represented by the formula

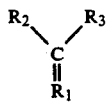

or a pharmaceutically acceptable salt thereof wherein
$R_1$ is $N-C\equiv N$;
$R_2$ is the structure

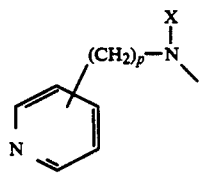

wherein X is H or $C_{1-10}$ alkyl and p is an integer from zero to 10; morpholinyl; indolinyl; isoindolinyl; substituted indolinyl or isoindolinyl wherein the substituent is alkyl having 1 to 4 carbon atoms; indanyl; substituted indanyl wherein the substituent is amino; 1,2,3,4-tetrahydroisoquinolinyl; substituted 1,2,3,4-tetrahydroisoquinolinyl wherein the substituent is alkyl having 1 to 4 carbon atoms; or 1,2,4,5-tetrahydro-3-benzazepin-3-yl and
$R_3$ is the structure

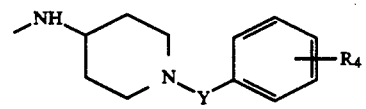

wherein Y is alkyl having 1 to 6 carbon atoms wherein one of the alkyls may be replaced by oxygen and $R_4$ is hydrogen, nitro, alkyl having 1 to 6 carbon atoms, alkoxy wherein the alkyl has 1 to 6 carbon atoms or halogen selected from chloro, fluoro or bromo.

The invention further relates to pharmaceutical compositions comprising a compound of Formula I. Such compounds and compositions have usefulness as cardiac arrhythmias. The invention also relates to a method of treating cardiac arrhythmias in a mammal in need of such treatment.

A preferred embodiment of the present invention is a compound of the formula

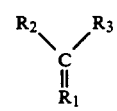

or a pharmaceutically acceptable salt, thereof, wherein
$R_1$ is $N-C\equiv N$;
$R_2$ is 1,2,3,4-tetrahydroisoquinolinyl or substituted 1,2,3,4-tetrahydroisoquinolinyl wherein the substituent is alkyl having 1 to 4 carbon atoms; and
$R_3$ is the structure

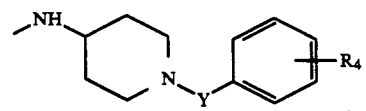

wherein Y is alkyl having 1 to 6 carbon atoms wherein one of the alkyls may be replaced by oxygen and $R_4$ is hydrogen, nitro, alkyl having 1 to 6 carbon atoms, alkoxy wherein the alkyl has 1 to 6 carbon atoms or halogen selected from chloro, fluoro or bromo.

Exemplifying this embodiment are the following compounds:
N-cyano-1,2,3,4-tetrahydro-N'-[1-[(4-methoxyphenyl)-methyl]-4-piperidinyl]-2-isoquinolinecarboximidamide;
N-cyano-1,2,3,4-tetrahydro-N'-[1-(phenylmethyl)-4-piperidinyl]-2-isoquinolinecarboximidamide;
N-cyano-3,4-dihydro-1-1-methyl-N'-[1-(phenylmethyl)-4-piperidinyl]-2(1H)-isoquinolinecarboximidamide, monohydrochloride;
N-cyano-3,4-dihydro-N'-[1-[1-[(4-nitrophenyl)methyl]-4-piperidinyl]-2(1H)-isoquinolinecarboximidamide;

N-cyano-N'-[1-[3-(4-fluorophenoxy)propyl]-4-piperidinyl]-3,4-dihydro-2(1H)-isoquinolinecarboximidamide;

N-cyano-3,4-dihydro-N'-[1-(3-phenylpropyl)-4-piperidinyl]-2(1H)-isoquinolinecarboximidamide;

N-cyano-3,4-dihydro-N'-[1-(phenylmethyl)-4-piperidinyl]-2(1H)-isoquinolinecarboximidamide and N-cyano-N'-[1-(phenylmethyl)-4-piperidinyl]-N'''-3-pyridinylguanidine A further preferred embodiment of the present invention is a compound of the formula

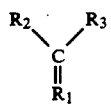

I or a pharmaceutically acceptable salt thereof, wherein
R₁ is N—C≡N;

R₂ is indolinyl; isoindolinyl; substituted indolinyl or isoindolinyl wherein the substituent is alkyl having 1 to 4 carbon atoms; indanyl; or substituted indanyl wherein the substituent is amino; and R₃ is

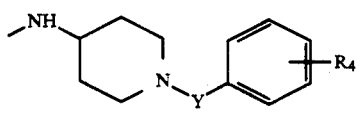

wherein Y is alkyl having 1 to 6 carbon atoms wherein one of the alkyls may be replaced by oxygen and R₄ is hydrogen, nitro, alkyl having 1 to 6 carbon atoms, alkoxy wherein the alkyl has 1 to 6 carbon atoms or halogen selected from chloro, fluoro or bromo.

Exemplifying this embodiment are the following compounds:

N-cyano-N'-(1,3-dihydro-2H-inden-2-yl)-N'''-[1-(phenylmethyl)-4-piperidinyl]guanidine;

N-cyano-N'-(2,3-dihydro-1H-inden-1-yl)-N'''-[1-(phenylmethyl)-4-piperidinyl]guanidine; and N-cyano-2,3-dihydro-N'-[1-(phenylmethyl)-4-piperidinyl]-2-1H-isoindolecarboximidamide.

As used herein, the term "alkyl" refers to straight chain or branched chain hydrocarbon group having 1 to 10 carbon atoms. Illustrative of such alkyl groups are methyl ethyl, propyl, isopropyl, butyl, isobutyl, pentyl, neopentyl, hexyl and isohexyl.

As used herein, the term "alkoxy having 1 to 6 carbon atoms" includes straight or branched chain ethers. Illustrative of such groups are methoxy, ethoxy, propoxy, butoxy and isopropoxy.

As used herein, the term "halogen" refers to chloro (Cl), fluoro (F), bromo (Br) and iodo (I).

As used herein, the term "morpholinyl refers to a six carbon saturated ring wherein two of the carbons are replaced by oxygen and nitrogen. This substituent is represented by the following structure

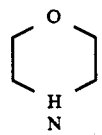

As used herein, the term "indolinyl" refers to a five carbon saturated ring wherein one of the carbon atoms is replaced by nitrogen which is fused to a benzene ring. This substituent is represented by the following structure.

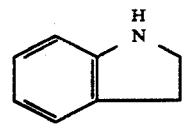

As used herein, the term "1,2,3,4-tetrahydro isoquinolinyl" refers to a six carbon saturated ring wherein one of the carbon atoms is replaced by nitrogen which is fused to a benzene ring. This substituent is represented by the following structure

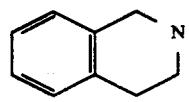

As used herein, the term "1,2,4,5-tetrahydro-3-benzazepin-3-yl" refers to a seven carbon saturated ring wherein one of the carbon atoms is replaced by nitrogen which is fused to a benzene ring. This substituent is represented by the following structure

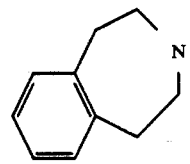

As used herein, the term "indanyl" refers to benzene ring which is fused to a saturated five carbon membered ring. This substituent is represented by the following structure

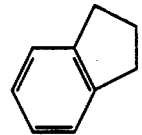

As used herein, the term "substituted indolinyl" or substituted 1,2,3,4-tetrahydro-isoquinolinyl" refers to the ring structures as defined above wherein substitution as defined earlier can be to any available atom on either ring.

The compounds as shown in Formula I can exist in various isomeric forms and all such isomeric forms are meant to be included. Tautomeric forms are also included as well as pharmaceutically acceptable salts of such isomers and tautomers.

In the structures and formulas herein, the bond drawn across a bond of an aromatic ring can be to any available atom on the aromatic ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

The term "pharmacologically effective amount" shall mean that amount of a drug or pharmaceutical agent that will elicit the biological or medical response of a tissue, system or animal that is being sought by a researcher or clinician.

The term "cardiac arrhythmia" is defined to mean any variation from the normal rhythm of the heartbeat, including, without limitation, sinus arrhythmia, premature heartbeat, heartblock, fibrillation, flutter, pulsus alternans, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

DETAILED DESCRIPTION OF THE INVENTION

The compounds of Formula I wherein $R_1$ is $N\equiv CN$ and $R_2$ and $R_3$ are described as before can be prepared by the procedure outlined by Scheme I.

Diphenylcyanocarbonimidate is reacted with $R_2$ wherein $R_2$ is described as before in the presence of acetonitrile. The resulting mixture is then stirred at room temperature for 1 to 4 hours in a high pressure environment (20,000 psi to 200,000 psi). The resulting product is then reacted with $R_3$ wherein $R_3$ is described as before at room temperature with stirring in a high pressure environment (20,000 psi to 200,000 psi) to give the compounds of Formula I wherein $R_1$ is $N-C\equiv N$ and $R_2$ and $R_3$ are described as before.

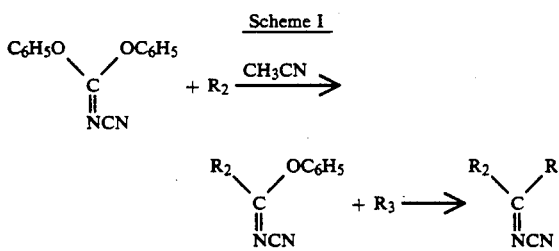

$R_2$ and $R_2$ are defined as before.

This invention also relates to a method of treating cardiac arrhythmias and more specifically, a method of treatment involving the administration of compounds of Formula I.

For the treatment of cardiac arrhythmias compounds of Formula I may be administered orally, parenterally, or by inhalation spray or rectally in dosage unit formulations containing conventional non-toxic pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus dosage regimen may vary widely. Dosage levels of the order from about 0.1 mg to about 100 mg per kilogram of body weight per day are useful in the treatment of the above-indicated conditions (from about 10 mg to about 500 mg per patient per day). For oral administration a daily dose of from about 0.1 to 100 mg/Kg body weight, particularly from about 1 to 50 mg/Kg body weight may be appropriate. For administration by injection a preferred daily dose would be from about 0.1 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention

EXAMPLE 1

Preparation of

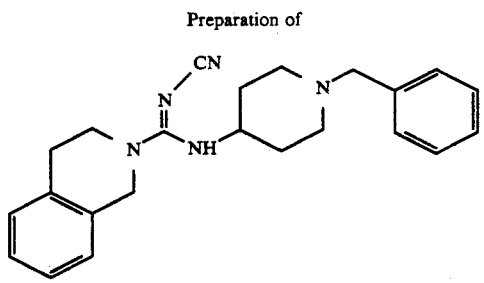

N-Cyano-1,2,3,4-tetrahydro-N'-[1-(phenylmethyl)-4-piperidinyl]-2-isoquinolinecarboximidamide 5 mmole of diphenylcyanocarbonimidate (M.W. 238) in 15 ml of acetonitrile was added to 5 mmole of 1,2,3,4-tetrahydroisoquinoline at room temperature. After four hours of stirring at room temperature 5 mmole of 4-amino-1-benzyl piperidine was added to the reaction and stirring continued for an additional 2 hours. The mixture was then placed in a high pressure environment (20,000 psi) for 17 hours. The solution was evaporated and the residue was separated and purified by column chromatography (toulene:ethylacetate:triethylamine, 40:60:1).

The resulting product had the following properties: m.p. 130–132° C.
Anal. Calcd. for $C_{23}H_{27}N_5$:

|   | Theory | Found |
|---|--------|-------|
| C | 73.96  | 73.75 |
| H | 7.39   | 7.29  |
| N | 18.75  | 18.40 |

$^1$HNMR: 1.5–1.65(m, 2H), 2.0–2.08(m, 2H), 2.11–2.18(m, 2H), 2.80–2.90(m, 2H), 2.97(m, 2H), 3.49(s, 2H), 3.70(m, 2H), 3.95(m, 1), 4.61(s, 2H), 7.1–7.32(m,9H).

IR: 1520 cm$^{-1}$, 1570 cm$^{-1}$, 2160 cm$^{-1}$ (in CHCl$_3$).

EXAMPLE 2

Preparation of

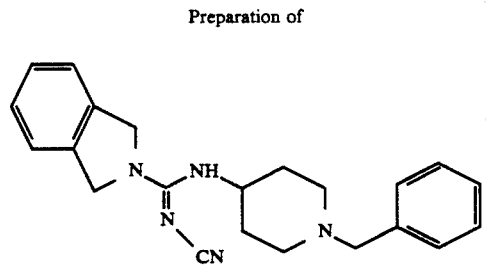

N-Cyano-2,3-dihydro-N'[1-(phenylmethyl)-4-piperidinyl]-2-1H-isoindolecarboximidamide The title compound was prepared in the manner of Example 1: Substituting indoline for 1,2,3,4-tetrahydroisoquinoline. The resulting product had the following properties: m.p. 191–192° C.;
Anal. Calcd. for $C_{22}H_{25}N_5$.

|   | Theory | Found |
|---|--------|-------|
| C | 73.51  | 73.13 |
| H | 7.01   | 7.14  |
| N | 19.48  | 19.29 |

$^1$HNMR (CDCl$_3$) δ, 1.48–1.57(m, 2H), 1.68–1.7(m, 2H), 2.04–2.12(m, 2H), 2.15–2.22(m, 2H), 2.80–2.90(m, 2H), 3.52(s, 2H), 4.09–4.15(m, 1H), 4.39–4.12(m, 1H), 4.90(s, 4H), 7.21–7.35(m, 9H).

EXAMPLE 3

Preparation of

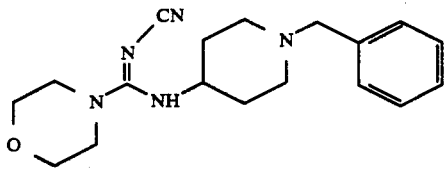

N-Cyano-N'-[1-(phenylmethyl)-4-piperidinyl]-4-morpholinecarboximidamide

The title compound was prepared in the manner of Example 1: Substituting morpholine for 1,2,3,4-tetrahydroisoquinoline. The resulting product had the following properties: m.p. 163–165° C.;
Anal. Calcd. $C_{18}H_{25}N_5$

|   | Theory | Found |
|---|--------|-------|
| C | 66.03  | 65.86 |
| H | 7.70   | 7.78  |
| N | 21.39  | 21.08 |

$^1$HNMR (CDCl$_3$) δ, 1.40–1.60(m, 2H), 1.90–2.22(m, 4H), 2.75–2.90(m, 2H), 3.41–3.50((m, 4H), 3.50 (s, 2H), 3.70–3.78(m, 4H), 3.80–3.95(m, 1H), 4.50–4.65(m, 2H), 7.25–7.35(m, 5H).

EXAMPLE 4

Preparation of

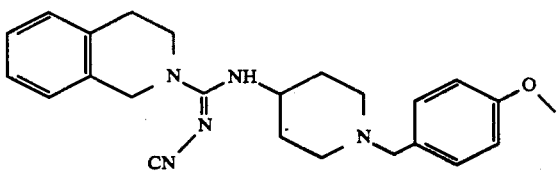

N-Cyano-1,2,3,4-tetrahydro-N'-[1-[(4-methoxyphenyl)-methyl]-4-piperidinyl]-2-isoquinolinecarboximidamide The title compound was prepared in the manner of Example 1: Substituting 4-amino-4-methoxyphenylmethyl piperidine for 4-amino-1-benzyl piperidine. The resulting product had the following properties: m.p. 135–137° C.;

|   | Theory | Found |
|---|--------|-------|
| C | 71.04  | 71.13 |
| H | 7.33   | 7.23  |
| N | 16.98  | 16.67 |

¹HNMR (CDCl₃) δ, 1.45-2.15(m, 2H), 1.80-2.25(m, 4H), 2.75-2.90(m, 2H), 2.90-3.0(m, 2H), 3.44(s, 2H), 3.69(s, 2H), 3.79(s, 3H), 4.58(s, 2H), 4.79-4.85(m, 2H), 6.85(d, J=8Z), 7.1-7.25(m, 4H), 7.24(d, J=8Z).

EXAMPLE 5

Preparation of

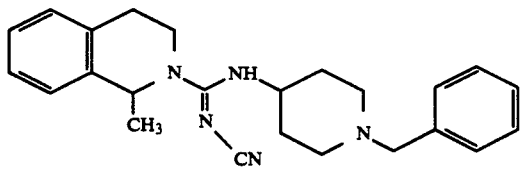

N-cyano-3,4-dihydro-1-methyl-N'-[1-(phenylmethyl)-4-piperidinyl]-2(1H)-isoquinolinecarboximidamide, monohydrochloride The title compound was prepared in the manner of Example 1: Substituting 2-methyl-3,4-dihydroisoquinoline for 1,2,3,4-tetrahydroisoquinoline. The resulting product had the following properties:
¹HNMR: 1.50(3H, d, J=5Z), 1.50-1.70(m, 2H), 1.90-2.20(m, 4H), 2.7-3.1(m, 4H), 3.3-3.5(m, 2H), 3.95-4.1(m, 2H), 5.2-5.3(m, 1H), 5.4-5.5(m, 1H), 7.0-7.3(m, 9H).
Anal. Calcd. for $C_{24}H_{34}N_5$

|   | Theory | Found |
|---|--------|-------|
| C | 62.75  | 63.07 |
| H | 7.69   | 7.30  |
| N | 14.63  | 14.26 |

IR: (CHCl₃), 1625, 1720, 2160, 3400cm⁻¹.

EXAMPLE 6

Preparation of

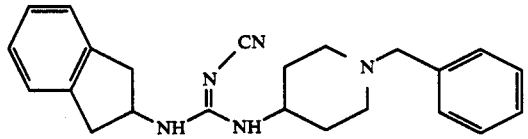

N-cyano-N'-(1,3-dihydro-2H-inden-2-yl)-N''-[1-(phenylmethyl)-4-piperidinyl]guanidine The title compound was prepared in the manner of Example 1: Substituting 1,3-dihydro-1H-inden-1-amine for 1,2,3,4-tetrahydroisoquinoline. The resulting product had the following properties: m.p. 138-140° C.;
Anal. Calcd. for $C_{23}H_{27}N_5$

|   | Theory | Found |
|---|--------|-------|
| C | 72.22  | 72.22 |
| H | 7.38   | 7.32  |
| N | 18.31  | 18.32 |

¹HNMR (CDCl₃), 1.4-1.6(m, 2H), 1.78-1.92(m, 2H), 2.0-2.2(m, 2H), 2.7-2.9(m,4H), 3.2-3.35(m, 2H), 3.47(s, 2H), 3.5-3.7(m, 1H), 4.4-4.6(m, 1H), 5.3-5.45(m, 1H), 5.75-5.58(m, 1H), 7.1-7.32(m, 9H).

EXAMPLE 7

Preparation of

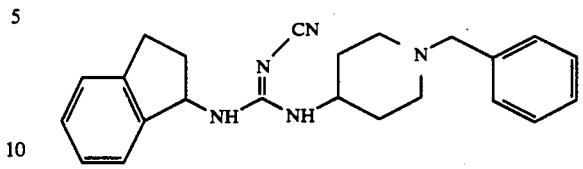

N-cyano-N'-(2,3-dihydro-1H-inden-1-yl)-N''-[1-(phenylmethyl)-4-piperidinyl]guanidine The title compound was prepared in the manner of Example 1: Substituting 2,3,-dihydro-1H-inden-1-amine for 1,2,3,4-tetrahydroisoquinoline. The resulting product had the following properties: m.p. 159-160° C.;
Anal. Calcd. for $C_{23}H_{27}N_5$

|   | Theory | Found |
|---|--------|-------|
| C | 73.96  | 74.02 |
| H | 7.29   | 7.47  |
| N | 18.75  | 18.65 |

¹HNMR: 1.4-1.6(m, 2H), 1.8-2.0(m, 3H), 2.02-2.2(m, 2H), 2.5-2.62(m, 1H), 2.65-3.1(m, 4H), 3.46(s, 2H), 3.49-3.6(m, 1H), 5.1(m, 1H), 5.1-5.2(m, 1H), 5.8-5.9(m, 1H), 7.2-7.4(m, 9H), IR(CDCl₃), 1580, 2160, 3280 cm⁻¹.

EXAMPLE 8

Preparation of

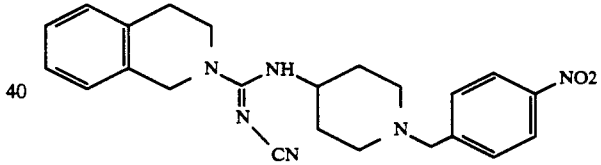

N-cyano-3,4-dihydro-N'-[1-[(4-nitrophenyl)methyl]-4-piperidinyl]-2(1H)-isoquinolinecarboximidamide The title compound was prepared in the manner of Example 1: Substituting 4-amino-1-3-nitrobenzylpiperidine for 4-amino-1-benzyl piperidine. The resulting product had the following properties: m.p 214-215° C.
Anal. Calcd. for $C_{23}H_{26}N_6$

|   | Theory | Found |
|---|--------|-------|
| C | 65.17  | 65.13 |
| H | 6.32   | 6.34  |
| N | 19.83  | 19.74 |

¹HNMR: 1.4-1.65(m, 2), 2.0-2.3(m, 4), 2.7-2.9(m, 2), 2.94-3.02(m, 2), 3.6(s, 2), 3.68-3.74(m, 2), 3.9-4.1(sm, 1), 4.4-4.51(m, 1), 4.61(s, 2), 7.1-7.27(m, 4), 7.48(d, J=10Z), 8.17(d, J=10Z)
IR: (CHCl₃), 1340, 1510, 1570, 2150, 3220 cm⁻¹.

EXAMPLE 9

Preparation of

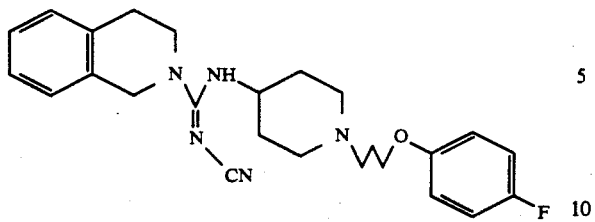

N-cyano-N'-[1-[3-4-fluorophenoxy)propyl]-4-piperidinyl]-3,4-dihydro-2(1H)-isoquinolinecarboximidamide The title compound was prepared in the manner of Example 1: Substituting 4-fluorophenoxy propyl-4-amino piperidine for 4-amino-1-benzyl piperidine. The resulting product had the following properties: m.p. 129–130° C.;

Anal. Calcd. for C$_{25}$H$_{39}$N$_5$

|   | Theory | Found |
|---|--------|-------|
| C | 68.94  | 68.57 |
| H | 6.94   | 6.97  |
| N | 16.08  | 16.05 |

$^1$HNMR: 1.48–1.51(m,2H), 1.88–2.0(m, 2H), 2.0–2.22(m, 4H), 2.5–2.56(m, 2H), 2.8–3.02(m, 4H), 3.68–3.72(m, 2H), 3.9–4.02(m, 3H), 4.61(s, 2H), 6.72–6.86(m, 2H), 6.90–7.00(m, 2H), 7.1–7.3(m, 4H).

EXAMPLE 10

Preparation of

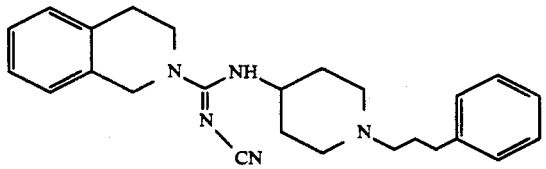

N-cyano-3,4-dihydro-N'-[1-(3-phenylpropyl)-4-piperidinyl]-2(1H)-isoquinolinecarboximidamide The title compound was prepared in the manner of Example 1: Substituting 3-phenylpropyl-4-amino piperidine for 4-amino-1-benzyl piperidine. The resulting product had the following properties: m.p. 122–124° C.;

Anal. Calcd. for C$_{25}$H$_{31}$N$_5$

|   | Theory | Found |
|---|--------|-------|
| C | 74.78  | 74.74 |
| H | 7.78   | 7.83  |
| N | 17.44  | 17.41 |

$^1$HNMR: 1.5–1.7(m 4H), 1.7–1.85(m, 2H), 1.9–2.1(m, 2H), 2.30–2.40(m, 2H), 2.55–2.63(m, 2H), 2.8–3.0(m, 4H), 3.67–3.72(m, 2H), 3.88–3.92(m, 1H), 4.62(s, 2H), 5.32–5.45(m, 1H), 7.0–7.3(m, 9H).

EXAMPLE 11

Preparation of

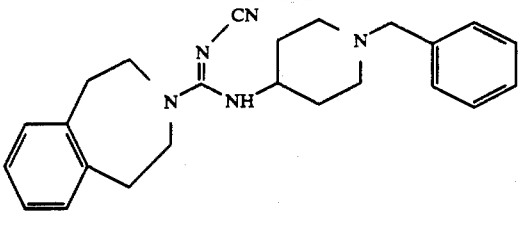

N-cyano-1,2,4,5-tetrahydro-N'-[1-(phenylmethyl)-4-piperidinyl]-3H-3-benzazepine-3-carboximidamide The title compound was prepared in the manner of Example 1: Substituting benzazepine for 1,2,3,4-tetrahydroisoquinoline. The resulting product had the following properties: m.p. 192–194° C.;

Anal. Calcd. for C$_{24}$H$_{29}$N$_5$

|   | Theory | Found |
|---|--------|-------|
| C | 74.39  | 74.14 |
| H | 7.54   | 7.52  |
| N | 18.07  | 18.04 |

$^1$HNMR: (CDCl$_3$), 1.49–1.61(m, 2H), 1.96–2.08(m, 2H), 2.1–2.23(m, 2H), 2.8–2.9(m, 2H), 2.93–3.06(m, 2H), 3.52(s, 2H), 3.6–3.7(m, 4H), 3.9–4.01(m, 1H), 4.6–4.72(m, 1H), 7.1–7.4(m, 9H).

EXAMPLE 12

Preparation of

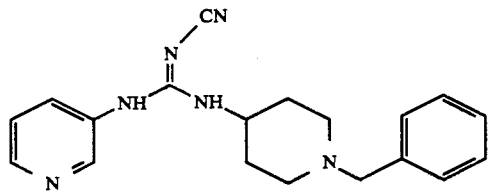

N-cyano-N'-[1-(phenylmethyl)-4-piperidinyl]-N"-3-pyridinylguanidine

The title compound was prepared in the manner of Example 1: Substituting 3-pyridine for the 1,2,3,4-tetrahydroisoguinoline. The resulting product had the following properties: m.p. 173–174° C.;

Anal. Calcd. for C$_{19}$H$_{22}$N$_6$

|   | Theory | Found |
|---|--------|-------|
| C | 68.24  | 68.08 |
| H | 6.63   | 6.77  |
| N | 25.13  | 24.88 |

$^1$HNMR (CDCl$_3$), δ (ppm), 1.3–1.55(m, 2H), 1.8–2.0(m, 2H), 2.01–2.15(m, 2H), 2.7–2.82(m, 2H), 3.47(s, 2H), 3.79(m, 1H), 5.36(m, 1H), 7.2–7.35(m, 5H), 7.64(m, 1H), 8.38(m, 1H), 8.49d, J=6Z, 1H).

EXAMPLE 13

Guinea pigs, of either sex weighing between 200 to 350 g are acutely sacrificed and the right ventricular papillary muscle is isolated. A sample of a given test compound is added using an in vitro tissue bath. Concentrations used are generally $3 \times 10^{31}$ $^5$M, but may also be as low as $3 \times 10^{-7}$M. Changes in refractory peiod are measured before and after adding 1 concentration (usually $3 \times 10^{-5}$M, as noted above) of a test compound to the bath. One hour is allowed for drug equilibration. A compound is considered active (Class III) if an increase in ventricular refractory period is 30 msec or more (at $3 \times 10^{-5}$ M).

| Compound | Concentration (M) | Change (msec) |
|---|---|---|
| H$_2$O | 0 | 8 |
| Disopyramide | $3 \times 10^{-5}$ | 20 |
| Clofilium | $3 \times 10^{-5}$ | 24 |
| Example 1 | $3 \times 10^{-5}$ | 45 |
| Example 3 | $3 \times 10^{-5}$ | 30 |
| Example 4 | $3 \times 10^{-6}$ | 50 |
| Example 6 | $3 \times 10^{-5}$ | 40 |
| Example 7 | $3 \times 10^{-5}$ | 70 |
| Example 8 | $3 \times 10^{-6}$ | 65 |

What I claim is:

1. A compound of the formula

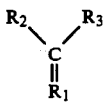

or a pharmaceutically acceptable salt thereof, wherein
R$_1$ is N—C≡N;
R$_2$ is isoindolinyl; indolinyl; substituted indolinyl or isoindolinyl wherein the substituent is alkyl having 1 to 4 carbon atoms; 1,2,3,4-tetrahydroisoquinolinyl; or substituted 1,2,3,4-tetrahydroisoquinolinyl wherein the substituent is alkyl having 1 to 4 carbon atoms;
R$_3$ is the structure

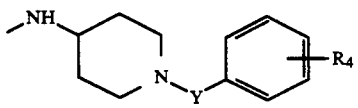

wherein Y is alkyl having 1 to 6 carbon atoms wherein one of the alkyls may be replaced by oxygen and R$_4$ is hydrogen, nitro, alkyl having 1 to 6 carbon atoms, alkoxy wherein the alkyl has 1 to 6 carbon atoms or halogen selected from chloro, fluoro or bromo.

2. A compound according to claim 1 of the formula

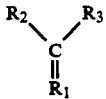

or a pharmaceutically acceptable salt thereof, wherein
R$_1$ is N—C≡N;
R$_2$ 1,2,3,4-tetrahydroisoquinolinyl or substituted 1,2,3,4-tetrahydroisoquinolinyl wherein the substituent is alkyl having 1 to 4 carbon atoms; and
R$_3$ is the structure

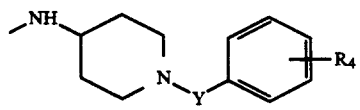

wherein Y is alkyl having 1 to 6 carbon atoms wherein one of the alkyls may be replaced by oxygen and R$_4$ is hydrogen, nitro, alkyl having 1 to 6 carbon atoms, alkoxy wherein the alkyl has 1 to 6 carbon atoms or halogen selected from chloro, fluoro or bromo.

3. A compound according to claim 1 of the formula

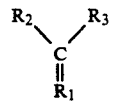

or a pharmaceutically acceptable salt thereof, wherein
R$_1$ is N—C≡N;
R$_2$ is isoindolinyl; indolinyl; or substituted indolinyl or isoindolinyl wherein the substituent is alkyl having 1 to 4 carbon atoms;
R$_3$ is the structure

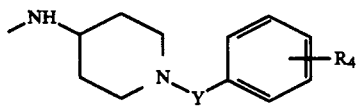

wherein Y is alkyl having 1 to 6 carbon atoms wherein one of the alkyls may be replaced by oxygen and R$_4$ is hydrogen, nitro, alkyl having 1 to 6 carbon atoms, alkoxy wherein the alkyl has 1 to 6 carbon atoms or halogen selected from chloro, fluoro or bromo.

4. A compound according to claim 2 which is N-cyano-1,2,3,4-tetrahydro-N'-[1-[(4-methoxyphenyl)methyl]-4-piperidinyl]-2-isoquinolinecarboximidamide.

5. A compound according to claim 2 which is N-cyano-1,2,3,4-tetrahydro-N'-[1-(phenylmethyl)-4-piperidinyl]-2-isoquinolinecarboximidamide.

6. A compound according to claim 2 which is N-cyano-3,4-dihydro-N'-[1-[1-[(4-nitrophenyl)methyl]-4-piperidinyl]-2(1H)-isoquinolinecarboximidamide.

7. A compound according to claim 2 which is N-cyano-3,4-dihydro-1-methyl-N'-[1-(phenylmethyl)-4-piperidinyl]-2(1H)-isoquinolinecarboximidamide, monohydrochloride.

8. A compound according to claim 2 which is N-cyano-N'-[1-[3-(4-fluorophenoxy)propyl]-4-piperidinyl]-3,4-dihydro-2(1H)-isoquinolinecarboximidamide.

9. A compound according to claim 2 which is N-cyano-3,4-dihydro-N'-[1-(3-phenylpropyl)-4-piperidinyl]-2(1H)-isoquinolinecarboximidamide.

10. A compound according to claim 3 which is N-cyano-2,3-dihydro-N'-[1-(phenylmethyl)-4-piperidinyl]-2-1H-isoindolecarboximidamide.

11. A pharmaceutical composition useful for heating cardiac arrhythmias comprising an effective amount of at least one compound according to claim 1, together with one or more non-toxic pharmaceutically acceptable carriers.

12. A pharmaceutical composition according to claim 11 wherein the compound is N-cyano-1,2,3,4-tetrahydro-N'-[1-(phenylmethyl)-4-piperidinyl]-2-isoquinolinecarboximidamide.

13. A method of treating cardiac arrhythmias in mammals comprising administering a therapeutically effective dose of at least one compound of claim 1 to a mammal in need of such treatment.

14. A method according to claim 13 wherein the compound is N-cyano-1,2,3,4-tetrahydro-N'-[1-(phenylmethyl)-4-piperidinyl]-2-isoquinolinecarboximidamide.

* * * * *

UNITED STATES PATENT AND TRADEMARK OFFICE
CERTIFICATE OF CORRECTION

PATENT NO. : 5,132,311
DATED : July 21, 1992
INVENTOR(S) : Chi-Dean Liang

It is certified that error appears in the above-identified patent and that said Letters Patent is hereby corrected as shown below:

Column 2, line 64, reading "dihydro-1-1-methyl" should read -- dihydro-1-methyl --.

Column 11, line 13, reading "[1-[3-4-" should read -- [1-[ 3-(4- --.

Column 12, line 68, reading "3X10$^{31}$ $^5$M," should read -- 3X10$^{-5}$ M, --.

Column 13, line 57, reading "R$_2$ 1,2,3," should read -- R$_2$ is 1,2,3, --.

Column 14, line 16, reading "atoms;" should read -- atoms; and --.

Signed and Sealed this

Thirtieth Day of November, 1993

Attest:

BRUCE LEHMAN

Attesting Officer

Commissioner of Patents and Trademarks